United States Patent [19]

Szoka, Jr.

[11] Patent Number: 5,567,434
[45] Date of Patent: Oct. 22, 1996

[54] PREPARATION OF LIPOSOME AND LIPID COMPLEX COMPOSITIONS

[75] Inventor: Francis C. Szoka, Jr., San Francisco, Calif.

[73] Assignee: The Regents of the University of California, Oakland, Calif.

[21] Appl. No.: 480,227

[22] Filed: Jun. 7, 1995

Related U.S. Application Data

[60] Division of Ser. No. 179,291, Jan. 10, 1994, which is a continuation-in-part of Ser. No. 741,937, Aug. 8, 1991, Pat. No. 5,277,914, which is a continuation-in-part of Ser. No. 605,155, Oct. 29, 1990, Pat. No. 5,077,057, which is a continuation of Ser. No. 334,055, Apr. 5, 1989, abandoned, which is a continuation-in-part of Ser. No. 332,609, Mar. 31, 1989, abandoned.

[51] Int. Cl.$^6$ .......................... A61K 9/127; A61K 51/12; B01J 13/02
[52] U.S. Cl. .................. 424/450; 424/1.21; 264/4.1; 264/4.3; 264/4.6; 264/4.7; 436/829
[58] Field of Search .................. 424/1.21, 450, 424/484; 264/4.1, 4.3, 4.6, 4.7; 436/829

[56] References Cited

U.S. PATENT DOCUMENTS 5,077,057  10/1990  Szoka, Jr. ............................. 424/450
5,277,914   8/1991  Szoka, Jr. ............................. 424/450

*Primary Examiner*—Carlos Azpuru
*Attorney, Agent, or Firm*—Crosby, Heafey, Roach & May

[57] ABSTRACT

Liposome and lipidic particle formulations of compounds are prepared by dissolving in a solution of liposome-forming lipids in an aprotic solvent such as DMSO, optionally containing a lipid-solubilizing amount of a lower alkanol, and either injecting the resulting solution into an aqueous solution, or the aqueous solution into the resulting solution. The resulting liposome or lipidic particle suspension may then be dialyzed or otherwise concentrated. This method is particularly useful for compounds which are poorly-soluble in aqueous solution, but is generally useful for any compound or combination of compounds which can be dissolved in the aprotic solvent or aprotic solvent/lower alkanol mixture.

4 Claims, 8 Drawing Sheets

PREPARATION OF LIPOSOME AND LIPID COMPLEX COMPOSITIONS

CROSS-REFERENCE TO RELATED APPLICATIONS

This is a divisional of U.S. patent application Ser. No. 08/179,291, filed Jan. 10, 1994, which is a continuation-in-part of U.S. patent application Ser. No. 08/741,937, filed 8 Aug. 1991, now U.S. Pat. No. 5,277,914 which is a continuation-in-part of U.S. patent application Ser. No. 07/605,155, filed 29 Oct. 1990, now U.S. Pat. No. 5,077,057, which is a continuation of U.S. patent application Ser. No. 334,055, filed 5 Apr. 1989, now abandoned, which is a continuation-in-part of U.S. patent application Ser. No. 332,609, filed 31 Mar. 1989, now abandoned.

TECHNICAL FIELD

This invention relates to the fields of pharmaceutical compositions, and the delivery of therapeutically, pharmaceutically or diagnostically useful compounds. This invention also relates to the production of liposomes and lipid particles having a defined particle size.

BACKGROUND OF THE INVENTION

Liposomes are small vesicles composed of amphipathic lipids arranged in spherical bilayers. Liposomes are usually classified as small unilamellar vesicles (SUV), large unilamellar vesicles (LUV), or multi-lamellar vesicles (MLV). SUVs and LUVs, by definition, have only one bilayer, whereas MLVs contain many concentric bilayers. Liposomes may be used to encapsulate various materials, by trapping hydrophilic compounds in the aqueous interior or between bilayers, or by trapping hydrophobic compounds within the bilayer.

Liposomes exhibit a wide variety of characteristics, depending upon their size, composition, and charge. For example, liposomes having a small percentage of unsaturated lipids tend to be slightly more permeable, while liposomes incorporating cholesterol or other sterols tend to be more rigid and less permeable. Liposomes may be positive, negative, or neutral in charge, depending on the hydrophilic group. For example, choline-based lipids impart a positive charge, phosphate- and sulfate-based lipids contribute a negative charge, and glycerol-based lipids and sterols are generally neutral in solution.

Liposomes have been employed to deliver biologically active material. See for example Allison, U.S. Pat. No. 4,053,585, which disclosed the administration of several antigens in negatively charged liposomes, optionally including killed *M. tuberculosis.* Fullerton et al., U.S. Pat. No. 4,261,975, disclosed the use of separated influenza membranes, with hemagglutinin spikes attached, which is bound to liposomes for use in influenza vaccines.

Liposomes have been used to encapsulate a large variety of compounds which exhibit poor aqueous solubility, or which exhibit unacceptable toxicity at therapeutic dosages. For example, amphotericin B is an antifungal antibiotic which is poorly soluble in water, alcohols, chloroform, and other common halocarbon solvents. While amphotericin B is an effective fungicide, it is also dangerously toxic at concentrations slightly above the therapeutic concentration. Encapsulation in liposomes appears to reduce the in vivo toxicity to mammalian cells, while leaving the fungicidal activity relatively unaltered (F. C. Szoka et al., *Antimicrob Agents Chemother* (1987) 31:421–29). The effects on cytotoxicity and fungicidal activity were dependent upon the particular liposome composition, liposomal structure (e.g., SUV, MLV, etc.), and method of preparation.

Phospholipid vesicles (liposomes) can be formed by a variety of techniques that, in general, start with "dry" lipids that are introduced into an aqueous phase (D. Lasic, *J Theor Biol* (1987) 124:35–41). Once the lipid is hydrated, liposomes form spontaneously. Techniques have been developed to control the number of lamellae in the liposomes and to produce a defined particle size. The available procedures are satisfactory for most applications where small amounts of material are needed (G. Gregoriadis, "Liposome Technology" I–III (Boca Raton, Fla., CRC Press, Inc.), 1984). However, for the manufacture of vesicles on a large scale, the lipid hydration step can be a severe constraint on vesicle production.

To accelerate the lipid hydration step, the lipids can be dissolved in an organic solvent and injected into the aqueous phase. This permits a continuous production of vesicles since the solvent can be removed by dialysis or evaporation. Using ethanol as the solvent, unilamellar liposomes of defined size can be formed by injection (S. Batzri et al., *Biochem Biophys Acta* (1973) 298:1015–1019; J. Kremer et al., *Biochemistry* (1977) 16:3932–3935). This procedure generates unilamellar vesicles as long as the lipid concentration in the ethanol is below 40 mM and the final ethanol concentration in the aqueous suspension is less than about 10% (F. Boller et al., EPO 87306202.0, filed 14 Jul. 1987). These two factors limit the concentration of defined sized liposomes formed by ethanol injection to about 4 mM. This is a rather dilute solution of liposomes; for water soluble compounds the encapsulation efficiency is poor, while for lipid soluble compounds large volumes are required to obtain a sufficient quantity of material. Because of these limitations, ethanol injection has not been widely employed for making lipid vesicles (D. Lichtenberg, et al., in "Methods of Biochemical Analysis" (D. Glick, ed., John Wiley & Sons, N.Y. (1988)), 35:337–462).

Lipid particles are complexes of an amphipathic lipid with another molecule, in a defined ratio, which result in a supramolecular structure or particle. The principal difference between a liposome and a lipidic particle is that a liposome has a continuous bilayer of lipid surrounding an aqueous core, whereas a lipidic particle does not. Because of this difference, in most cases, lipidic particles cannot encapsulate water soluble molecules. Lipidic particles can range in size from about 5 nm to greater than 1,000 nm. The size of the final lipidic particle depends upon the composition and the method of preparation. Examples of lipidic particles are the lipid emulsions (S. Ljungberg et al., *Acta Pharmaceutica Suecica* (1970) 7:435–40), lipoproteins (A. Gotto et al., *Meth Enzymol* (1986) 129:783–89), and iscoms (K. Lovgren et al., *J Immunol Meth* (1987) 98:137–43).

DISCLOSURE OF THE INVENTION

A new method is disclosed for preparing liposomal suspensions containing compounds which exhibit poor solubility in water, alcohols, and halogenated hydrocarbon solvents. The method provides a high, efficient encapsulation rate. Additionally, the method is suitable for practice on an industrial manufacturing scale, and may be practiced as a continuous process. Other significant advantages of this method include: the formation of high concentrations of liposomes, defined diameter preparations, simplicity, speed of particle formation, ease of scaling to large volumes, and the possibility to encapsulate compounds that have poor water/organic solubility but high solubility in aprotic solvents.

The method comprises first preparing solutions, one containing a suitable lipid in an aprotic solvent such as DMSO, optionally containing a solubilizing amount of a lower alcohol and the other an aqueous solution of appropriate ionic strength and drug composition. Compounds that are poorly soluble are included in the lipid solution while compounds that are aqueous-soluble are included in the aqueous solution. The method next comprises injecting the resulting lipid solution through a suitably sized aperture into the stirred or mixed aqueous solution. Alternatively, the appropriate aqueous solution may be injected through the aperture into the stirred or mixed aprotic solvent. These processes are suitable for continuous production. The resulting liposomal suspension may be dialyzed or otherwise concentrated, if desired.

MODES OF CARRYING OUT THE INVENTION

A. Definitions

Figure 1:
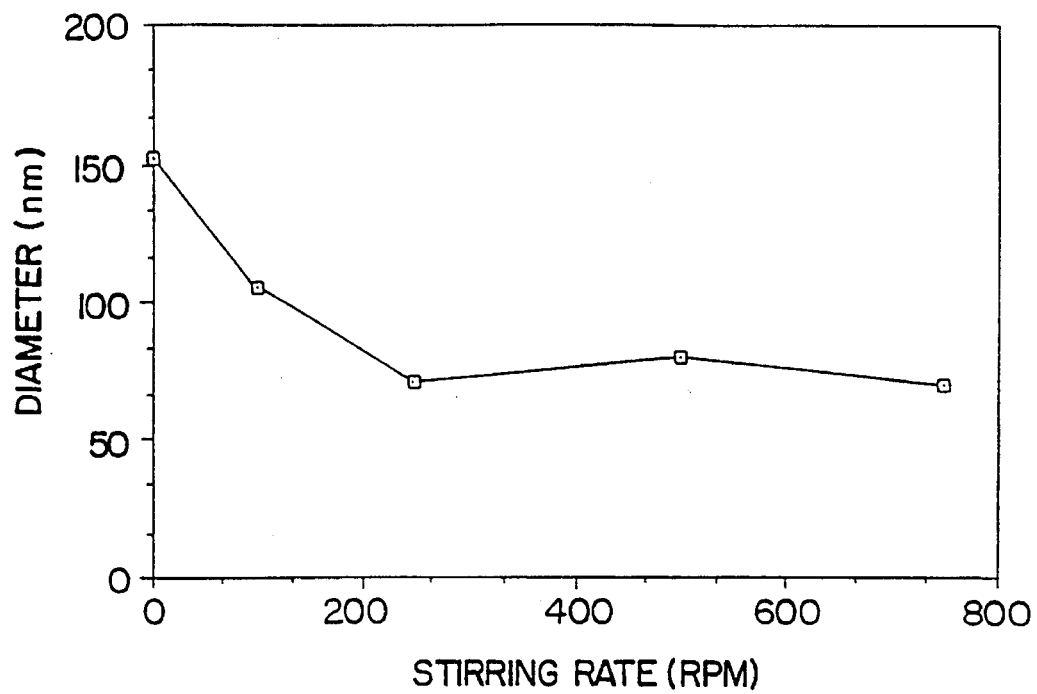
FIG. 1 depicts the effect of stirring rate on liposome diameter, as described in Example 1.

The term "poorly soluble compound" as used herein refers to compounds which appear to be very slightly soluble or substantially insoluble (less than about 1 mg/ml) at physiologic temperature and pH in standard solvents. "Standard solvents" includes water and aqueous solutions, lower alcohols (for example, methanol, ethanol, propanol, isopropanol, butanols, t-butanol, and the like). Suitable poorly soluble compounds include cisplatin, doxorubicin, epinephrine, mebendazole, niridazole, taxol, polyene antibiotics such as amphotericin B, nystatin, and primaricin, and the like.

The term "suitable lipid" as used herein refers to an amphipathic compound which is capable of liposome formation, and is substantially nontoxic when administered at the necessary concentrations as liposomes. Suitable lipids generally have a polar or hydrophilic end, and a nonpolar or hydrophobic end. Suitable lipids include without limitation egg phosphatidylcholine (EPC), egg phosphatidylglycerol (EPG), dipalmitoylphosphatidylcholine (DPPC), cholesterol (Chol), cholesterol sulfate and its salts (CS), cholesterol hemisuccinate and its salts (Chems), cholesterol phosphate and its salts (CP), cholesterol phthalate, cholesterylphosphorylcholine, 3,6,9-trioxaoctan-1-ol-cholesteryl-3e-ol, dimyristoylphosphatidylglycerol (DMPG), dimyristolyphosphatidylcholine (DMPC), hydrogenated soy phosphatidylcholine (HSPC), and other hydroxy-cholesterol or aminocholesterol derivatives (see; e.g., K. R. Patel et al., *Biochim Biophys Acta* (1985) 814:256–64).

The term "encapsulating amount" refers to the amount of lipid necessary to encapsulate the poorly soluble compound and form liposomes or lipidic particles of appropriate size. Preferably, the average liposome or lipidic particle's size is less than 10,000 nm in diameter, more preferably less than 5,000 nm, and still more preferably about 20–600 nm. The encapsulating amount will depend upon the particular compound and process conditions selected, but will in general range from about 2:1 to about 1:100 compound:lipid, preferably about 1:1 to about 1:20.

The term "lipid-compound suspension of defined particle size" refers generically to complexes of the invention formed from a suitable lipid and a compound to be encapsulated or complexed. Lipid-compound suspensions of defined particle size include liposomes and lipidic particles which have a particles size distribution on the order of <10,000 nm in diameter, preferably <5,000 nm, and more preferably 20–600 nm.

The term "lipidic particle" as used herein refers to particles of undefined structure which consist of a suitable lipid and an encapsulated or complexed compound. Polyene antibiotics at high antibiotic:lipid ratios typically form lipidic particles rather than liposomes, due to the polyene structure and its interaction with the lipid. Lipidic particles may have a lamellar structure, but are not required to exhibit any definable structure. The structure of these particles is currently unknown.

The term "aprotic solvent" as used herein refers to solvents which are not hydrogen donors, and which do not include hydrocarbon or halogenated hydrocarbon solvent. Suitable aprotic solvents include dimethylsulfoxide (DMSO), dioxane, dimethylformamide (DMF), acetonitrile, 1,2-dimethoxyethane (DME), N,N-dimethylacetamide (DMA), sulfolane, gamma butyrolactone, 1-methyl-2-pyrrolidinone (MP), and methylpyrroline, preferably DMSO.

The term "lower alkanol" refers to compounds of the formula R—OH, where R is a fully saturated hydrocarbon radical having from one to six carbon atoms. Suitable lower alkanols include methanol, ethanol, n-propanol, isopropanol, n-butanol, and the like. Ethanol and methanol are presently preferred, particularly ethanol.

B. General Method

The compositions of the invention are produced by preparing a lipid solution in an aprotic solvent, along with an encapsulating amount of a suitable lipid and an aqueous solution of appropriate ionic strength. The aprotic solvent solution may additionally contain a lower alkanol if needed to solubilize the lipid. Poorly soluble compounds may be dissolved in the lipid solution while aqueous-soluble compounds may be dissolved in the aqueous solution. The resulting lipid solution is then extruded into the aqueous solution, with stirring, forming a liposome or lipidic particles suspension. The liposomes or lipidic-particle suspension may also be formed by extruding the aqueous solution into the aprotic solvent solution, with stirring. The suspension may be dialyzed or otherwise concentrated, if desired.

The aprotic solvent is selected from dimethylsulfoxide (DMSO), dioxane, dimethylformamide (DMF), acetonitrile, 1,2 -dimethoxyethane (DME), N,N-dimethylacetamide (DMA), sulfolane, gamma butyrolactone, 1-methyl-2-pyrrolidinone (MP), and methylpyrroline. DMSO is presently preferred.

The lipid concentration in the aprotic solvent solution will vary depending upon the particular lipid or lipid mixture selected. However, in the practice of the present invention, one may use lipid Concentrations ranging from about 2 mM to about 400 mM, preferably about 40–120 mM. The lipid solution preferably contains a lower alkanol, preferably ethanol or methanol, in a ratio of about 1:2 to 8:1 aprotic solvent:alkanol. Presently preferred solvent ratios are 1:1 to 7:3 DMSO:EtOH.

The poorly soluble compound is selected for its solubility in the aprotic solvent or aprotic solvent/lower alkanol mixture used. The ratio of compound to lipid used may range from about 2:1 to about 1:100 compound:lipid, preferably about 1:1 to about 1:20, depending on the compound employed. With polyene-type compounds such as amphotericin B, ratios of about 1:1 are presently preferred. Aqueous-soluble compounds are dissolved or suspended in the aqueous phase at a concentration appropriate for the desired compound:lipid ratio.

An injection solution is then injected into a receiving solution. That is, the compound/lipid solution (lipid solution) is then extruded or injected into a suitable aqueous solution (aqueous/compound solution), or the aqueous solution (aqueous/compound solution) is extruded or injected into the compound/lipid solution (lipid solution). The extrusion means may be a syringe, perforated plate or tube, or other appropriate device providing apertures of about 0.05 mm to about 5 mm, preferably about 0.8 mm. One may also use a sintered disk having a 0.1–50 μm nominal retention size. The method of the invention is not sensitive to the rate of extrusion; a rate of about 0.5–10 ml/min/aperture is suggested for the sake of convenience. The method of the invention is also not particularly sensitive to stirring rate. However, the receiving solution is preferably stirred at a rate of at least 150 rpm. For the lipid soluble compounds, the aqueous solution may contain small amounts of buffering compounds, preservatives, and the like, but the ionic strength should not exceed that obtained by about 1M NaCl, preferably not exceeding the ionic strength of a solution of about 0.1M NaCl, more preferably not exceeding the ionic strength of a solution of about 10 mM NaCl. The temperature of the aqueous phase will in general be between the transition temperature of the lipids employed, and the boiling point of the aprotic solvent/alkanol mixture. Preferably, the temperature will be in the range of about 25°–80° C., more preferably about 30°–60° C. The temperature of the lipid solution may range from the freezing point of the aprotic solvent/alkanol mixture to its boiling point, but in general is preferably about ambient temperature. The volume of the receiving solution is not particularly critical to the process of the invention, and is preferably minimized in order to facilitate concentration of the liposomes or lipidic particles after formation. In general, the ratio of lipid solution to aqueous solution may range from about 1:25 to about 1:1, preferably about 1:10 to about 1:15.

If desired, the liposome or lipidic particle suspension obtained may be concentrated by standard techniques, including centrifugation, dialysis, diafiltration, counter current dialysis, and the like.

The suspensions are used in a manner appropriate to the useful compound encapsulated. The suspensions may be used for therapeutic, diagnostic, or pharmaceutical purposes, or may be used in research. Where the compound is a pharmaceutically active compound, the suspensions of the invention are preferably administered parenterally, for example by intramuscular, subcutaneous, or intravenous injection. Other modes of administration include intraocular drops, intranasal spray or drops, topical salves, and the like. The mode of delivery determines the preferred lipid particle size. For example, lipid particles in the size range from 500 nm to 5,000 nm are useful for topical delivery while lipid particles less than 200 nm are useful for injection and may be purified by sterile filtration.

C. Examples

The examples presented below are provided as a further guide to the practitioner of ordinary skill in the art, and are not to be construed as limiting the invention in any way.

Methods and Materials

In the examples set forth below, egg phosphatidylcholine, egg phosphatidylglycerol, dipalmitoylphosphatidylcholine (DPPC) were obtained from Sigma Inc., St. Louis, Mo., as chloroform/ethanol solutions. Cholesterol, cholesterol sulfate (sodium salt), and cholesterol hemisuccinate (Tris salt) were obtained from Sigma as dry powders. In some experiments the EPC, dimyristoylphosphatidylglycerol, dimyristoylphosphatidylcholine and hydrogenated soy phosphatidylcholine (HSPC) used were obtained from Natterman, Cologne, as dry powders. Thin-layer chromatography on silica gel 60 (Merck) in a solvent system of chloroform/methanol/water (65/25/4) at high lipid loadings showed only one component for each of the above phospholipids. DL-α-tocopherol was from Serva. The cis-platinum was a product of Bristol Myers, Syracuse, N.Y. Doxorubicin was obtained from Farmitalia as the lyophilized powder containing lactose. The 1-methyl-2-pyrrolidinone, 1,2-dimethoxyethane, gamma butyrolactone, lactose, urea, amphotericin B (AmpB), nystatin and primaricin were obtained from Sigma. Other chemicals were reagent grade. The solvents, except as noted above, were obtained from Merck and were puriss or HPLC grade. Absolute ethanol (EtOH) was from Merck. Double-distilled deionized water was used in the preparation of all solutions.

Preparation of Lipid Stock Solutions

Lipids were either weighed into a round bottom flask of known weight or deposited from the chloroform/ethanol solution by removal of the solvent on a rotary evaporator. The lipids were placed under high vacuum at room temperature for 24 hours. The flasks were reweighed after this period and made up to a standard volume with dry ethanol in a volumetric flask to obtain the stock lipid concentrations. A clear stock solution of egg phosphatidylcholine containing 0.05 mole percent tocopherol under a nitrogen atmosphere was usually prepared at 300–400 mM by heating the ethanol solution to 60° C. DPPC and HSPC were dissolved, with heating, to 300 mM concentration. At this concentration the HSPC formed a gel when the temperature was reduced to 20° C. Anhydrous solvents were used in the preparation of all lipid solutions and precautions were taken to minimize the exposure of the solutions to the atmosphere. When other alcohols such as methanol (MeOH), propanol, isopropanol and tertiary butanol were used, egg phosphatidylcholine was dissolved at 400 mM by heating to 60° C. Mixtures of the alcohol lipid stock solution with the various other solvents were on a volume-to-volume basis by pipetting the alcoholic lipid solution into a volumetric flask and adding the second solvent to the indicated mark. Cholesterol was prepared in ethanol at 100 mM by heating to 60° C.; when cooled to room temperature, it would crystallize from solution. For certain experiments cholesterol was dissolved in 1-methyl-2-pyrrolidinone at a concentration of 364 mM. Cholesterol sulfate and Chems were dissolved in dimethylsulfoxide (DMSO) at a concentration of 71 mM. Mixtures of lipids were prepared from the stock solutions on a volume-to-volume basis. Lipid stocks were stored under a nitrogen atmosphere at −20 ° C. Phospholipid concentration of the final liposome preparations was determined by measuring the phosphorous concentration after acid digestion as described (G. Bartlett, *J Biol Chem* (1959) 234:466–468).

Injection System

A water-jacketed glass reaction vessel with a volume of 15 ml was used to contain the aqueous phase. The temperature of the vessel was maintained at 30° C., unless otherwise specified, by circulating water from a temperature-controlled water bath. The vessel was placed on a magnetic stirrer and a 1 cm magnetic stirring bar was positioned on the bottom of the receptor compartment. The spinning rate of the stirring bar was controlled by the rheostat on the magnetic stirrer and provided continuous mixing up to about 1000 rpm. Typical conditions for the solvent injection were as follows: 3 ml of aqueous receptor phase was placed in the vessel and the magnetic stirrer was spun at 750 rpm. The aqueous phase was allowed to equilibrate to the required temperature. A 0.5 ml gas-tight Hamilton syringe with a Teflon plunger was used for injections requiring less than 0.5 ml. A 3 ml plastic syringe was used for injections requiring between 0.5 ml and 3.0 ml. The syringe was positioned in the center of the vessel, directly over the magnetic stirring bar and tip of the syringe needle (25 gauge) was placed under the aqueous phase and about 2–4 mm above the stirring bar. In a typical experiment, 0.3 ml of lipid solution in the solvent was injected at a rate of 3.6 ml/min (5 s). This arrangement provided very rapid and thorough mixing of the lipid solution with the aqueous solution. Mixing, could be observed by placing a dye in the lipid solution and injecting it into the aqueous phase. The lipid suspension was stirred for 5 min, then removed from the vessel and placed in a dialysis bag. The sample was dialyzed versus 100 volumes of appropriate buffer changed twice over a 24 hour period. As it turns out, the system is quite robust and different injection conditions yield vesicles with similar diameters over a wide range of stirring rates, injection rates, temperatures, receptor volumes and aqueous:solvent ratios.

Determination of Vesicle Diameter

Vesicle diameter was measured by dynamic light scattering using a helium-neon 100 mW NEC gas laser and a Malvern K7027 correlator. At least three measurements were made for each determination. The diameter and polydispersity were reported as the mean of the three determinations.

Example 1

Parameters of Liposome Formation

The following experiments were conducted to determine the effects of process parameters on the final liposome products.

(A) Effect of Injection Conditions

The injection system was first examined using a dye dissolved in the solvent mixture. It was observed that placement of the syringe tip into the aqueous phase directly over the magnetic stirring bar gave rapid mixing. When 0.2 ml of a 70 mM EPC solution in DMSO:EtOH (7:3) was injected into 2 ml of water, a slightly opalescent suspension was produced as soon as the solvent mixed. In the absence of stirring, the vesicle diameter was 152 nm. As the stirring rate was increased to 250 rpm, the vesicle diameter decreased to 71 nm (FIG. 1). The diameter of the resulting vesicles remained constant as the stirring rate was further increased to 750 rpm (FIG. 1). Therefore in all ensuing experiments the stirring rate was maintained at 750 rpm.

Figure 2:
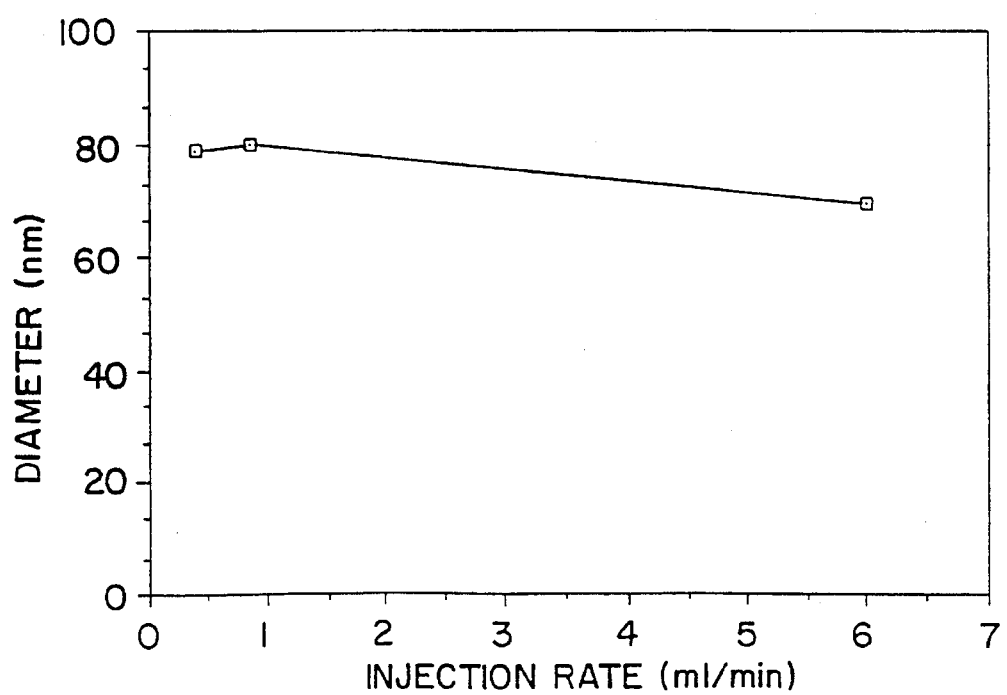
FIG. 2 depicts the effect of injection rate on liposome diameter.

The diameter of the resulting liposomes was relatively insensitive to the injection rate from 0.4 ml/min to 6 ml/min (FIG. 2). In all subsequent experiments the injection rate was between 2–6 ml/min.

Figure 3:
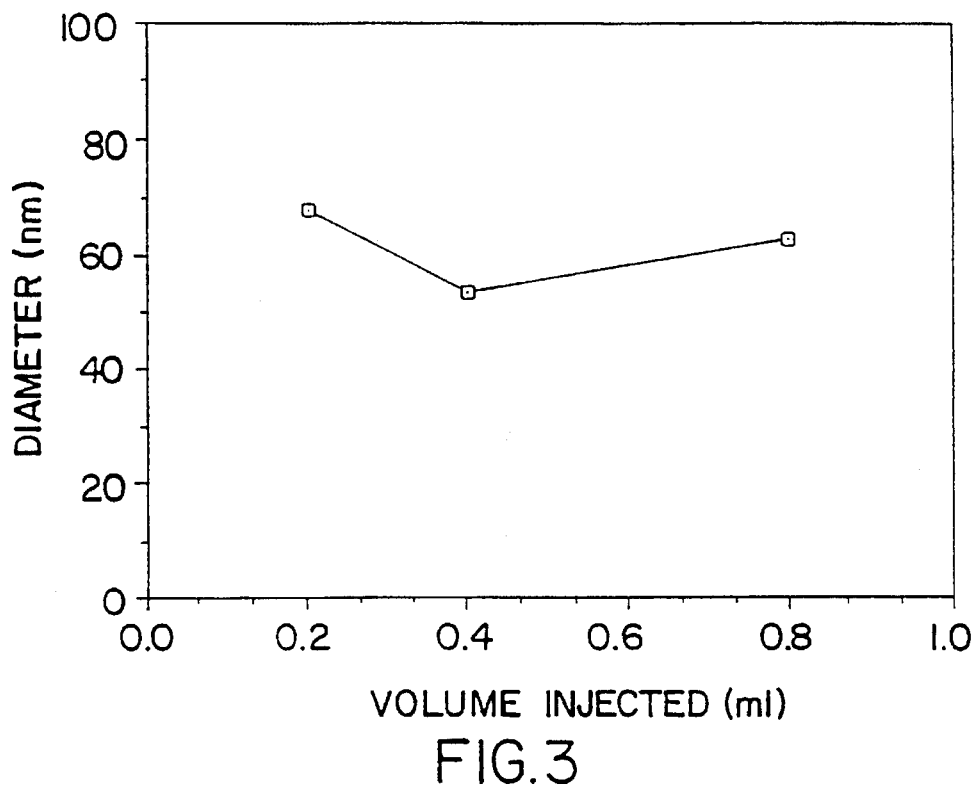
FIG. 3 depicts the effect of injection volume on liposome diameter.
Figure 4:
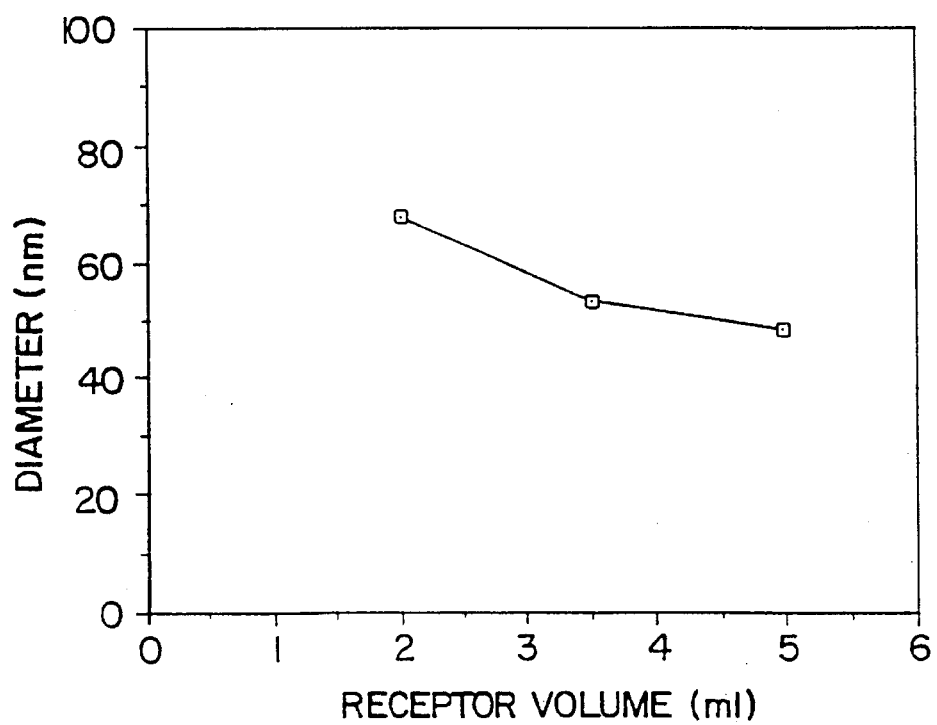
FIG. 4 depicts the effect of aqueous solution volume on liposome diameter.

When the aqueous phase volume was constant but the quantity of the lipid and solvent increased, the diameter of the resulting vesicles hardly changed (FIG. 3). When the volume of the aqueous phase was increased from 2 ml to 5 ml but the ratio of solvent to aqueous phase and final lipid concentration remained constant, vesicle diameter exhibited a slight decrease from 68 nm to 48 nm (FIG. 4). In all successive experiments, the aqueous volume was at least 3 ml and in most cases 4 ml.

Figure 5:
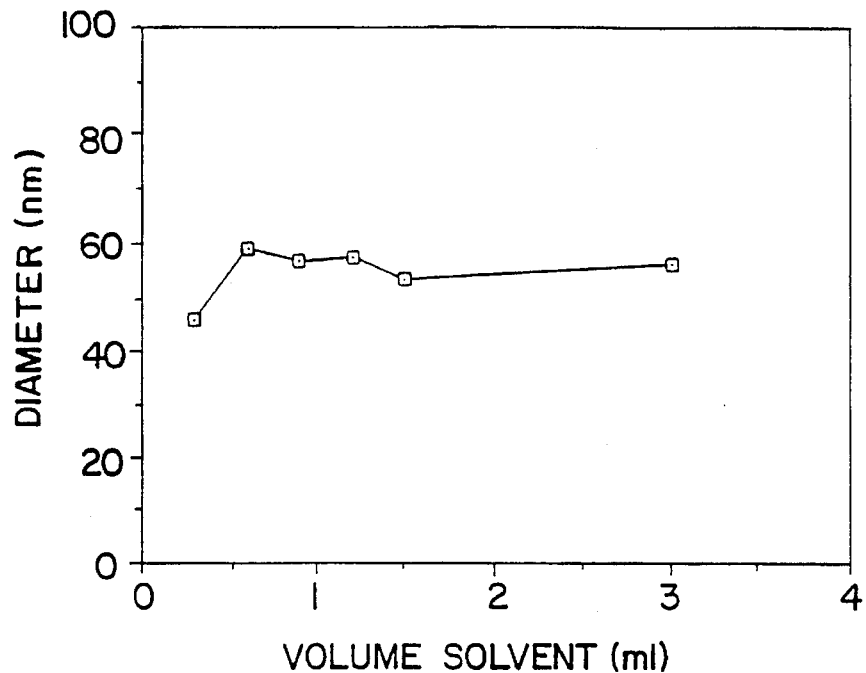
FIG. 5 depicts the effect of increasing aprotic solvent volume (at constant lipid concentration and aqueous solution volume) on liposome diameter.

If the amount of lipid injected and the aqueous phase remained constant but the volume of the solvent injected increased, the diameters of the resulting vesicles were unchanged (FIG. 5). This is in spite of the fact that at the highest concentration tested, the final mixture after injection contained 50% solvent.

Figure 6:
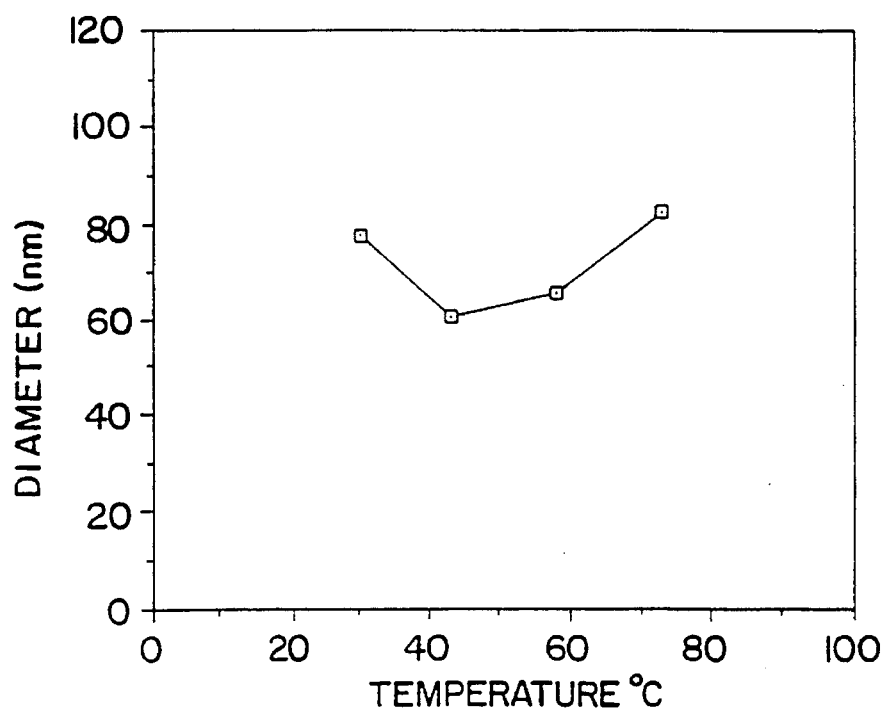
FIG. 6 depicts the effect of aqueous solution temperature on liposome diameter.

In these experiments the temperature of the aqueous phase was maintained at 30° C. However, varying the temperature of the aqueous phase from 30° to 80° C. had only a modest effect on the diameter of the resulting vesicles (FIG. 6). In all of the subsequent injection experiments, the temperature of the aqueous phase was regulated at 30° C. The lipids in the solvent mixture were used at room temperature (20°–24° C.).

Thus, initial experiments demonstrated that the diameter of vesicles formed during the solvent injection procedure was relatively unaffected by a large number of variables that could conceivably influence the injection system. Based upon these results, the standard injection conditions were as follows: lipid was injected at a rate of 2–6 ml/min into a 3–4 ml aqueous volume at 30° C. stirring at 750 rpm so that the final solvent to aqueous ratio was between 0.075 and 0.33. This robustness makes the procedure easy to set up with common laboratory equipment.

(B) Influence of Aqueous Phase

Figure 7:
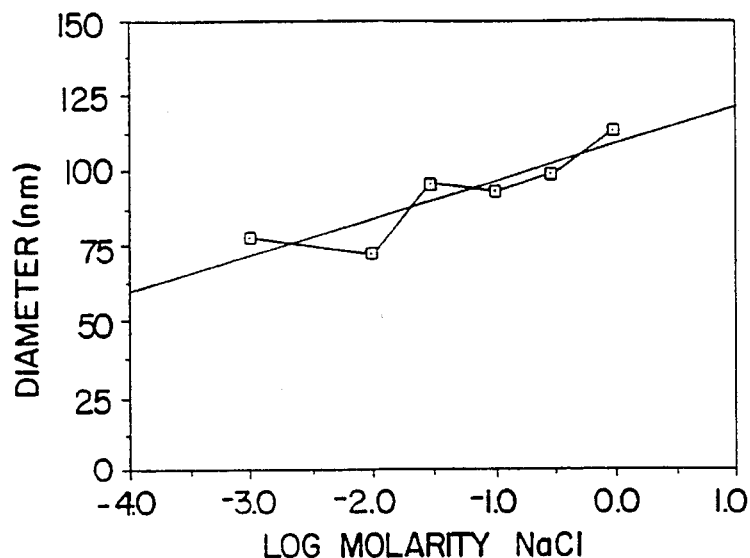
FIG. 7 depicts the effect of aqueous phase ionic strength on liposome diameter.

In a number of procedures for making liposomes, the properties of the aqueous phase during the formation of the liposome, such as ionic strength, pH and types of buffers, can influence the resulting liposomal properties (Lichtenberg, supra). A linear relationship was observed ($r^2=0.88$) between vesicle diameter and the logarithm of the NaCl molarity (FIG. 7). This apparent effect of the ionic strength on vesicle diameter was observed both times the complete titration from 0.001 to 1.0 mM salt was run. It was a consistent finding that when two or more preparations were compared, vesicles formed in the higher ionic strength aqueous phase had larger diameters, when all other conditions were the same.

Figure 8:
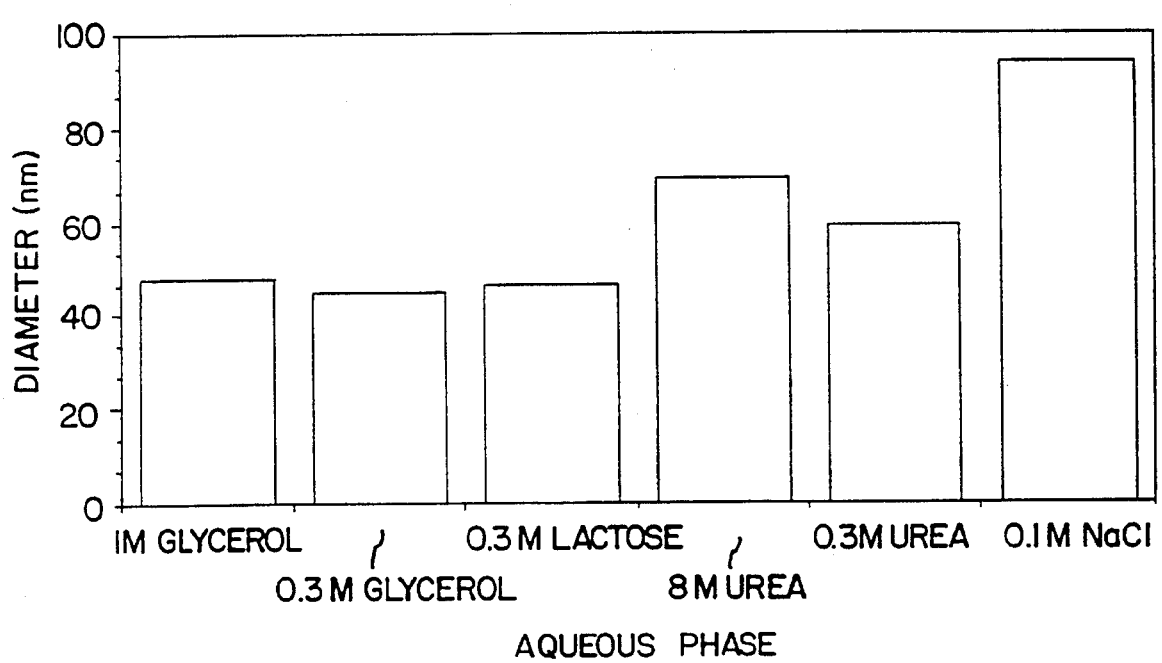
FIG. 8 depicts the effect of aqueous solution solute composition on liposome diameter.
Figure 9:
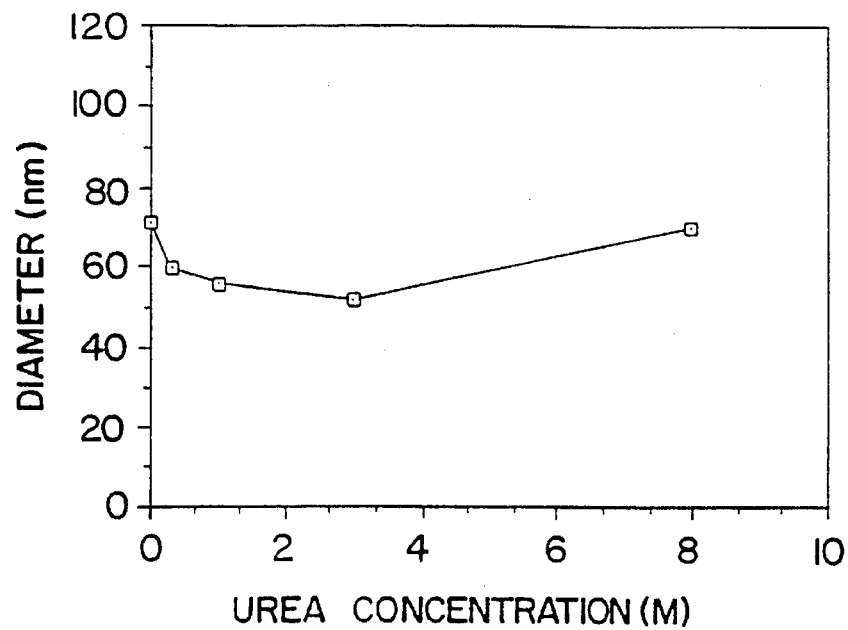
FIG. 9 depicts the effect of urea concentrations the aqueous solution on liposome diameter.

When nonionic solutes (glycerol, lactose or urea) were added to the aqueous phase, there was no effect on vesicle diameter (FIG. 8) even when the urea concentration was increased from 0 to 8M (FIG. 9). This suggests that the salt effect is due to a change of the ionic strength and not to a change in the osmolarity of the aqueous suspension.

Figure 10:
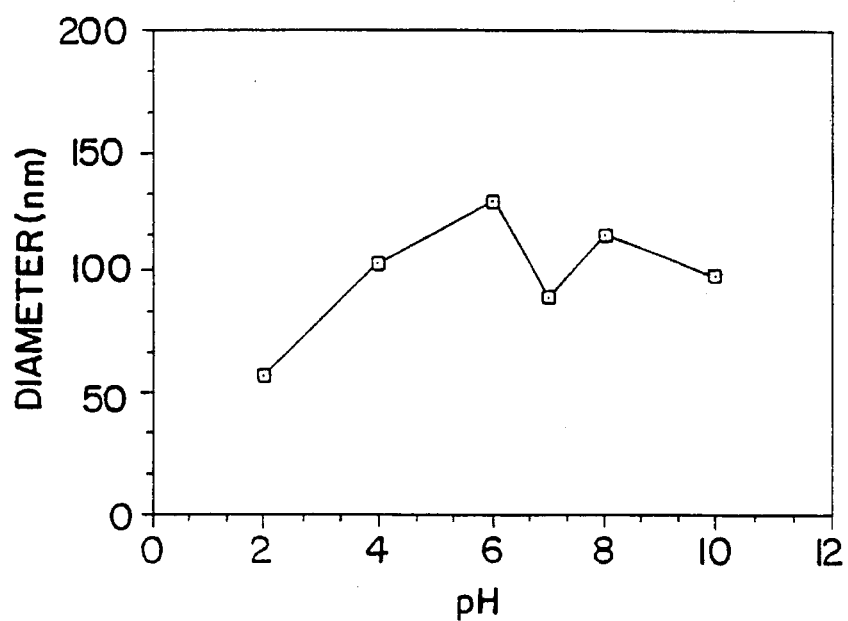
FIG. 10 depicts the effect of aqueous solution pH on liposome diameter.

Changes in the pH of the aqueous phase from pH 10 to pH 4, at a relatively constant ionic strength, had little effect on the diameter of the vesicles (FIG. 10). However, vesicles formed at pH 2.0 were appreciably smaller than vesicles formed at the higher pH values.

(C) Influence of Solvent Mixture

Figure 11:
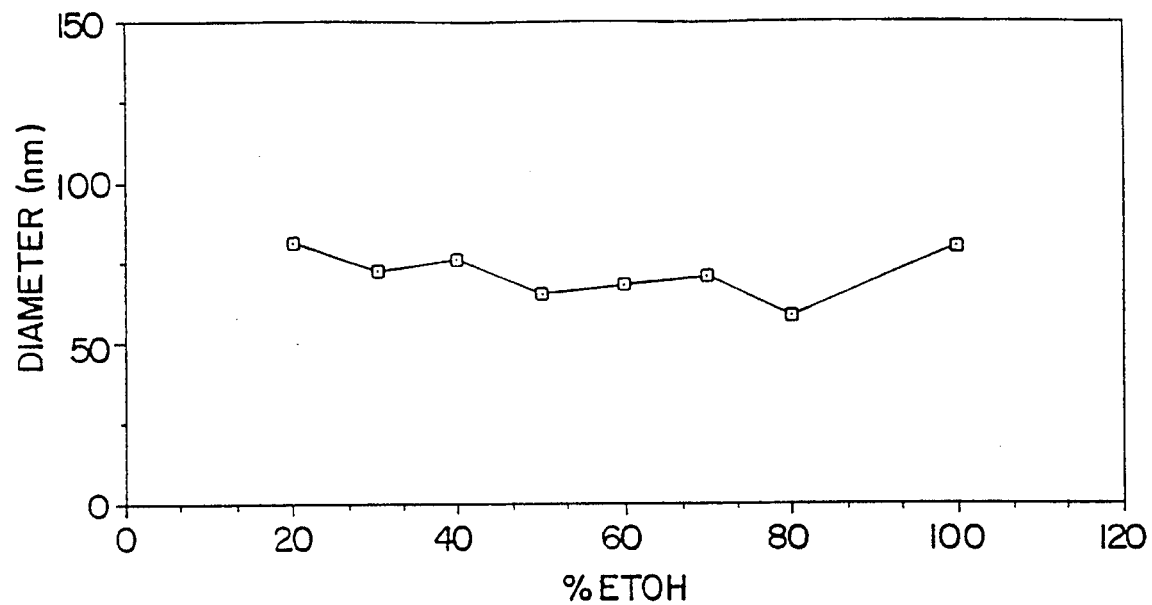
FIG. 11 depicts the effect of the ratio of EtOH to DMSO on liposome diameter.

Preliminary experiments indicated that the nature of the solvents and the lipid concentration in the solvent mixture influenced both the appearance of the lipid suspension and the vesicle diameters measured by light scattering. The effect of these two parameters were examined at the maximum lipid concentration (40 mM) where the EtOH injection method was reported to yield unilamellar vesicles (Kremer et al., *Biochemistry* (1977) 16:3932–3935) and at lipid concentrations two- to three-fold greater. Altering the ratio of DMSO:EtOH from 8:2 to absolute EtOH had no significant effect on the resulting vesicle diameters (FIG. 11).

Figure 12:
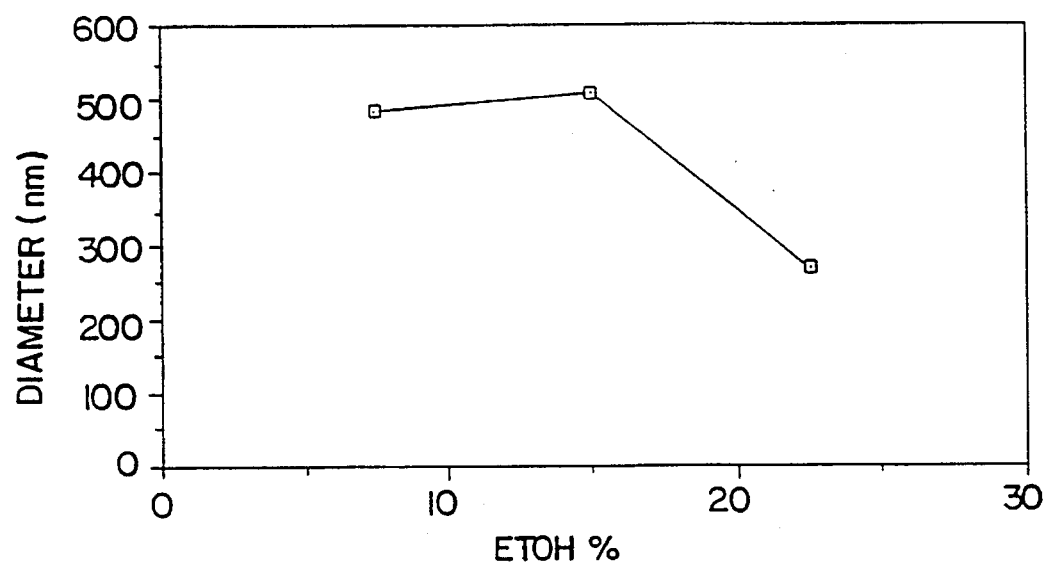
FIG. 12 depicts the effect of EtOH concentration following injection on liposome diameter.

In the classical EtOH injection technique (Batzri, supra; Kremer, supra) the final percentage of EtOH in the aqueous phase at constant lipid injected influenced the diameter of the resulting vesicles. This effect can be seen in FIG. 12 where vesicle diameter changes as the percentage of EtOH in the resulting suspension increases. For comparison, vesicles formed from a DMSO:EtOH mixture at the same lipid concentration at a final solvent percentage of 7.5 had a diameter of 93 nm versus 83 nm for the pure EtOH. As noted above, increasing the final solvent percentage to 50% when DMSO:EtOH mixture was used as a solvent hardly altered the vesicle diameter (FIG. 5).

Figure 13:
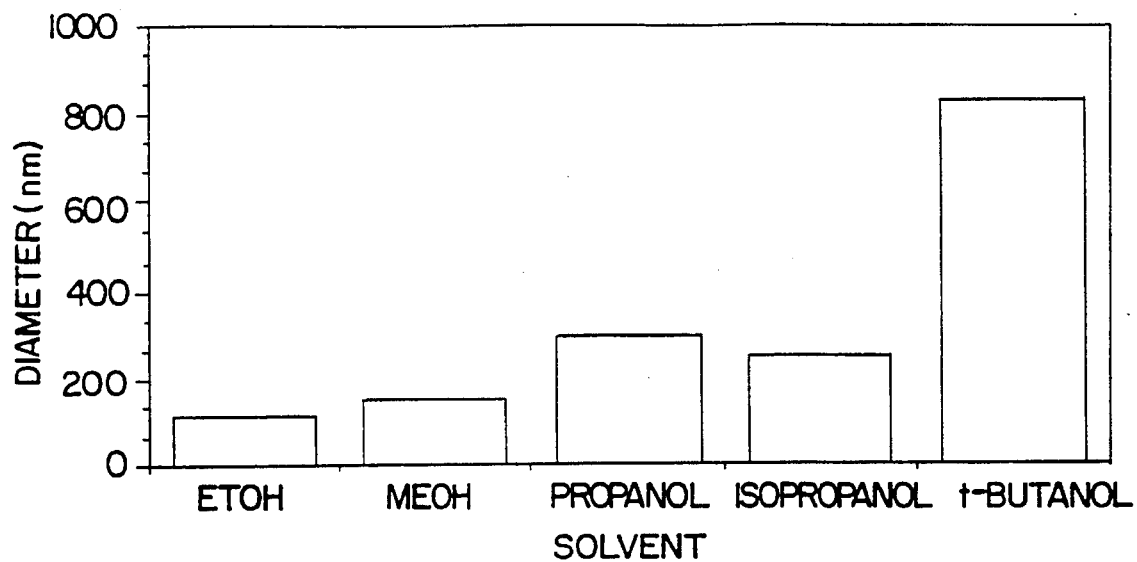
FIG. 13 depicts the effect of different alkanol/DMSO mixtures on liposome diameter.

Since a DMSO:EtOH ratio of 2:1 could solubilize lipids quite well, the effects of changing the alcohol at high lipid concentration on the vesicle diameters was examined (FIG. 13). At this lipid concentration, EtOH and MeOH mixed with DMSO provided the smallest diameter vesicles, 114 nm and 154 nm, respectively. Propanol and isopropanol DMSO mixtures yielded vesicles with significantly greater diameters (295 nm and 254 nm, respectively). Finally, tertiary butanol:DMSO mixtures yielded the greatest diameter vesicles, 832 nm. The latter three solvent mixtures produced vesicle suspensions that sedimented after dialysis. An examination of these three under the microscope revealed a mix of small structures and larger structures that had the classical MLV appearance (A. Bangham et al., *J. Mol Biol* (1965) 13:238–252).

Figure 14:
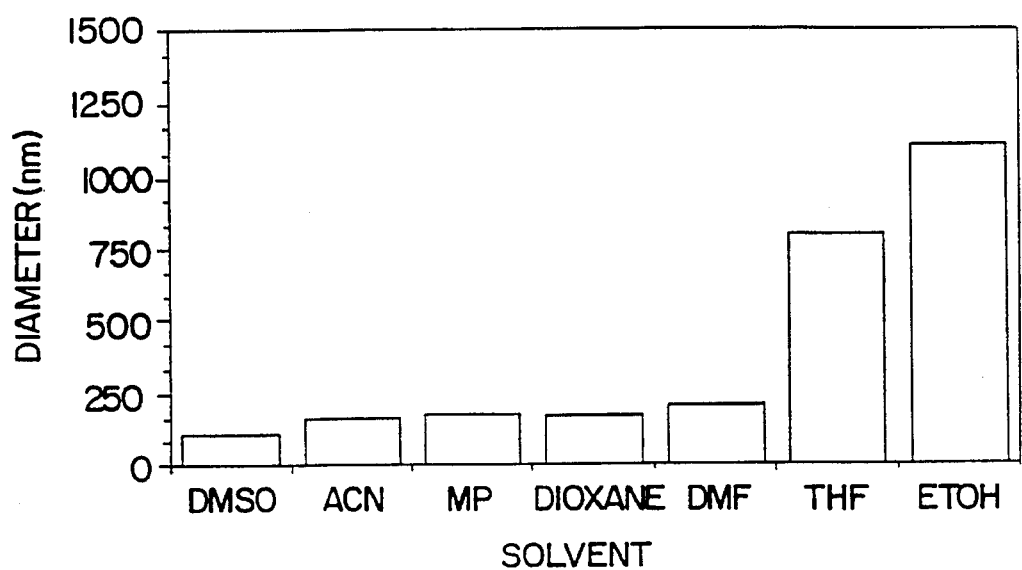
FIG. 14 depicts the effect of different aprotic solvents with EtOH on liposome diameter.

The aprotic cosolvent used with ethanol also influenced the diameter of the resulting vesicles (FIG. 14). DMSO as the cosolvent produced the smallest diameter vesicles (113 nm). Dioxane, dimethylformamide, acetonitrile and 1-methyl-2-pyrrolidinone produced vesicles in the 160–200 nm diameter range. Tetrahydrofuran/EtOH and pure EtOH lipid solutions produced vesicles with diameters greater than 800 nm (FIG. 14). After dialysis, these latter two liposome suspensions were composed of large MLV-like structures that were extensively aggregated when viewed under the light microscope.

(D) Influence of Lipid Concentration

Figure 15:
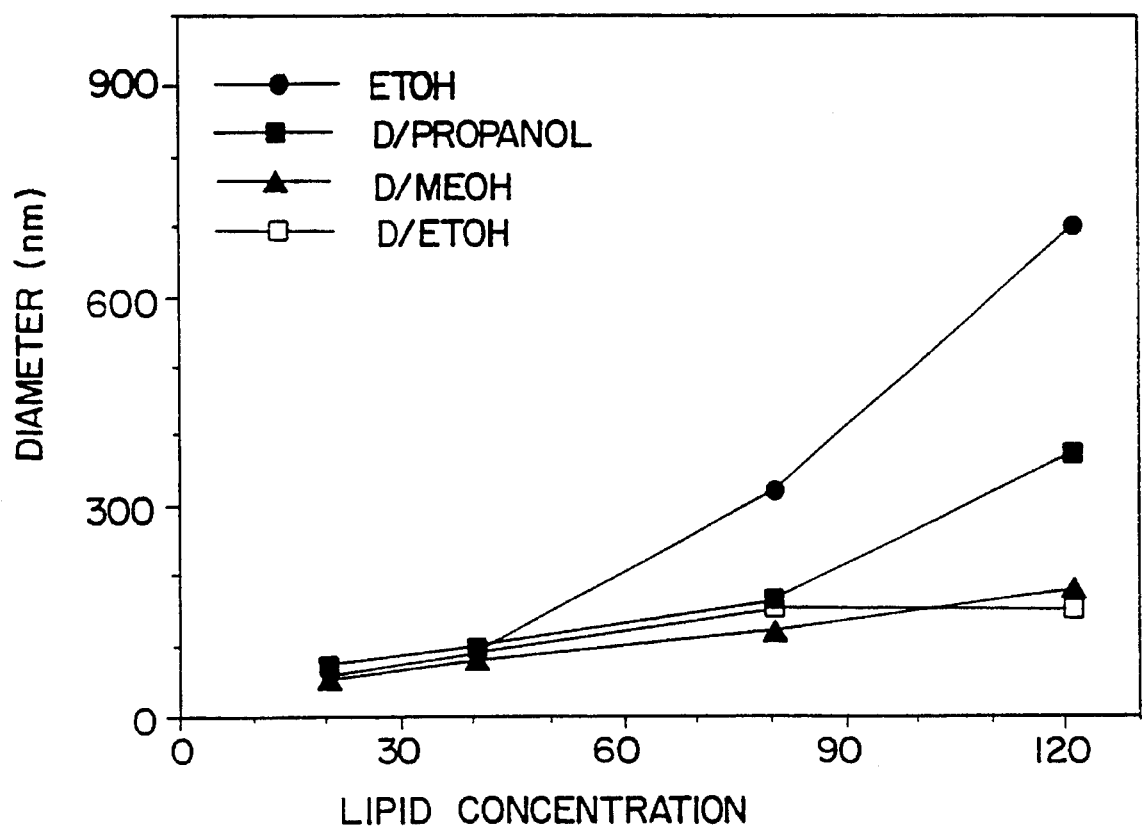
FIG. 15 depicts the effect of lipid concentration on liposome diameter for EtOH and three DMSO/alkanol mixtures.

An important parameter in the original EtOH injection method was the concentration of lipid in the EtOH (Kremer, supra). The effect of lipid concentration was examined in EtOH and three DMSO:alcohol (2:1) solvent mixtures: EtOH, MeOH and propanol (FIG. 15). As noted above, when the lipid concentration exceeds 40 mM in the EtOH, the resulting vesicle diameter increases considerably (Kremer, supra). Vesicle diameters were 83 nm at 40 mM and 690 nm at 121 mM. Although not previously mentioned, the polydispersity of the preparation also increases from 0.33 at 40 mM to 0.69 at 121 mM. The DMSO/propanol mixture also yielded a significant increase in vesicle diameter and polydispersity (0.24 to 0.59) of the preparation when the lipid concentration increased to 121 mM. The DMSO/EtOH and DMSO/MeOH mixtures formed vesicles with diameters of about 50 nm at the lowest lipid concentration used, to about 150 nm at the highest lipid concentration (FIG. 15). The polydispersity of the vesicle preparations over this same lipid concentration range varied from 0.250 to 0.370 for the EtOH and MeOH-containing solvent mixtures.

The increase in vesicle diameters as measured by light scattering at the higher lipid concentrations (FIG. 15) is also reflected in the appearance of the preparations. A very turbid suspension is visible with the EtOH and Propanol/DMSO mixtures at 121 mM lipid and a much less opalescent suspension arises with the EtOH/DMSO and MeOH/DMSO mixtures following injection.

Example 2

Encapsulation of Doxorubicin

An important compound for cancer chemotherapy is doxorubicin. A number of investigators have demonstrated that when this compound is administered as the liposome-encapsulated form, its toxicity in animals is reduced. All previously reported liposome preparations for encapsulation of doxorubicin have used a dry lipid hydration step, in spite of the low aqueous solubility of the drug at pH 7.4. Doxorubicin is very soluble in DMSO, so that it lends itself to the DMSO injection procedure of the invention.

Doxorubicin was dissolved in DMSO and added to an ethanol solution of EPG:EPC:Chol (7:3:6) to yield a final doxorubicin concentration of 6.2 mM and a final total lipid concentration of 96.4 mM in a DMSO:EtOH (7:3) solvent mixture. Lipid vesicles were formed by injecting 1 ml of the lipid-doxorubicin mixture into 2 ml of an aqueous phase consisting of 140 mM NaCl-10 mM Tris-HCl, pH 4.0, at 30° C. The lipid suspension was dialyzed for 2 h at room temperature against 100 volumes of 140 mM NaCl-10 mM Tris, pH 4.0 (NaCl-Tris). The liposome-encapsulated doxorubicin was separated from the nonencapsulated material by column chromatography on a 1×40 cm Sephadex® G-50 column eluted with NaCl-Tris. The amount of doxorubicin recovered in the vesicle peak was corrected for changes in volume during the procedure and compared to the initial amount injected to obtain an encapsulation efficiency. Doxorubicin concentration was measured spectrophotometrically at 480 nm following solubilization of the liposome/doxorubicin preparations with Triton® X-100 and heating.

The resulting vesicle diameter was 227 nm, and 41.2% of the doxorubicin was encapsulated in the vesicles.

Example 3

Preparation of Polyene Lipid Complexes (A) The preparation of amphotericin B liposomes or lipidic particles (R. New et al., *Antimicrob Chemotherap* (1987) 8:371–381; G. Lopez-Berestein et al., "Biophysics to Therapeutics" (M. Ostro, Ed. 1987) 253–76: F. Szoka et al., *Antimicrob Ag Chemotherap* (1987) 31:421–429) has always presented technical problems because of the low solubility of polyene antibiotics in most solvents (N. Rajagopalan et al., *J Parenteral Sci Tech* (1988) (42:97–102). Due to the limited solubility of the polyene antibiotics in most solvents, early preparations of the formulations required large amounts of solvents such as methanol (Lopez-Berestein, 1987). To decrease the amount of solvent used in the preparations, amphotericin B in DMSO had been added to dried films of lipid to form the amphotericin B liposomes (Szoka, supra). This did not yield small diameter preparations and required significant additional preparation steps, such as sonication, in order to provide a formulation suitable for use in animals.

The development of the method of the invention has made possible the simple preparation of these formulations. Not only are the polyene antibiotics soluble in DMSO, but so are Chems and CholSO$_4$. Cholesterol is exceedingly soluble in 1-methyl-2pyrrolidinone. Therefore, a solvent injection method was used to prepare polyene/sterol complexes. Preparations that contained up to 5 mM amphotericin B were easily prepared with a number of formulations (Tables 1–4). With the polyene antibiotics, more than 90% of the polyene was recovered in the preparations following extensive dialysis to remove nonassociated drug. These compositions were either 1:1 or 1:2 ratios of polyene:lipid, so that the weight percent of the active component in the formulation is quite high. Complexes with particle diameters less than 1000 nm could be formed from cholesterol, Chems, and CholSO$_4$ (Table 1). Three suitable component complexes containing DPPC and Chems or Chol were also formed (Table 2).

TABLE 1

Preparation of Amphotericin B/Single Lipid Complexes by Solvent Injection

| Lipid & Ratio[a] | Solvent[b] | Aqueous Phase | Diameter[c] (nm) |
|---|---|---|---|
| Chol 1:1 | DMSO:EtOH 7:3 | 10 mM Hepes | 451 |
| Chol 1:1 | DMSO:MP 1:1 | NaCl-Hepes | >1500 |
| Chems 1:1 | DMSO | NaCl-Hepes | >1500 |
| Chems 1:1 | DMSO | 10 mM Hepes | 90 |
| Chems 1:1[d] | DMSO | 10 mM Hepes | 160 |
| CholSO$_4$ 1:1 | DMSO | NaCl-Hepes | >1500 |
| CholSO$_4$ 1:1 | DMSO | 10 mM Hepes | 143 |
| DPPC 1:1 | DMSO:EtOH 7:3 | NaCl-Hepes | >1500 |
| DPPC 1:1 | DMSO:EtOH 7:3 | 10 mM Hepes | >1500 |
| DPPC 1:2 | DMSO:EtOH 7:3 | NaCl-Hepes | >1500 |

[a]amphotericin B:lipid ratio.
[b]Solvent volume was 0.25 ml injected into 3.0 ml of the indicated buffer at 30° C. The buffer pH was 7.4.
[c]Particle diameter was measured after dialysis in formation buffer. Values greater than 1500 nm indicate that large particle diameters were present that could not be accurately measured by dynamic light scattering. In all cases where the diameters were greater than 1500 nm, extensive aggregation and settling of the preparations in the dialysis bag were observed.
[d]Solvent volume was 1.0 ml injected into 3.0 ml of the indicated buffer.

TABLE 2

Preparation of Amphotericin B/Multiple Lipid Complexes by Solvent Injection

| Component Ratio[a] | Solvent[b] | Aqueous Phase | Diameter[c] (nm) |
|---|---|---|---|
| Chol:DPPC 1:1:1 | DMSO:EtOH 7:3 | 10 mM Hepes | 254 |
| Chol:DPPC 1:1:1 | DMSO:EtOH 7:3 | NaCl-Hepes | >1500 |
| Chems:EPC 1:1:1 | DMSO:EtOH 7:3 | NaCl-Hepes | >1500 |
| Chems:DPPC 1:1:1[d] | DMSO:EtOH 7:3 | 10 mM Hepes | 92 |
| Chems:DPPC 1:1:1[d] | DMSO:EtOH 7:3 | NaCl-Hepes | >1500 |
| Chems:HSPC 1:1:1 | DMSO:EtOH 7:3 | NaCl-Hepes | >1500 |

[a]amphotericin B:lipid ratio.
[b]Solvent volume was 0.25 ml injected into 3.0 ml of the, indicated buffer at 60° C. The buffer pH was 7.4.
[c]Particle diameter was measured after dialysis in formation buffer. Values greater than 1500 nm indicate that large particle diameters are present that cannot be accurately measured by dynamic light scattering. In all cases where the diameters were greater than 1500 nm, extensive aggregation and settling of the preparations in the dialysis bag were observed.
[d]Temperature of the aqueous phase was 30° C.

Solutions of the polyene antibiotics amphotericin B (30 mM) and nystatin (50 mM) were prepared in DMSO. The primaricin aqueous suspension obtained from Sigma was lyophilized and resuspended in various solvents. Primaricin was very soluble in DMSO, but after standing at room temperature for 2 h, a precipitate formed that could not be resuspended by warming the solution. A stable yellow solution of primaricin could be prepared in a 1:1 solvent mixture of DMSO:MP. The polyene antibiotics were combined with the various lipids in a solvent mixture of DMSO, DMSO:MP or DMSO:EtOH (7:3) and then injected into the aqueous phase. The preparations formed were transferred to a dialysis bag and dialyzed versus 100 volumes of distilled water, changed twice unless otherwise indicated. The ratio of the components, exact solvent mixtures and other conditions are given in the results. Samples of the preparations were dissolved in methanol and the polyene concentration determined spectrophotometrically (Szoka et al., supra): amphotericin B at 406 nm, nystatin at 306 nm and primaricin at 318 nm.

Preparations containing polyene antibiotics were sensitive to the ionic strength, pH and ratio of solvent to aqueous phase in the preparation (Tables 1, 3, 4). For instance, at low ionic strength (10 mM buffer) particle diameters less than 700 nm were obtained. When 0.1M NaCl was included in the aqueous buffer, all other conditions kept constant, the particle size became greater 1500 nm, and extensive aggregation was observed. This is a function of the polyene, since for a number of the lipids, particle diameters less than 200 nm were obtained upon injection of the lipid alone into the NaCl-Hepes buffer.

The pH of the receptor phase was also important in determining the particle size. In the case of the Chems:polyene complexes, the smallest particle sizes were obtained at pH $\geq 7$, whereas for CholSO$_4$:polyene complexes small diameters could be obtained at pH 4.0 and at pH >5 (Tables 3, 4).

TABLE 3

Preparation of Amphotericin B/Lipid Complexes by Solvent Injection

| Component Ratio[a] | pH[b] | Aqueous Phase | Diameter[c] (nm) |
|---|---|---|---|
| A:Chems 1:1.1 | 4.0 | 10 mM acetate | >1500 |
| A:Chems 1:1.1 | 7.0 | 10 mM Hepes | 111 |
| A:Chems 1:1.1 | 8.0 | 10 mM Hepes | 121 |
| A:CholSO$_4$ 1:1.1 | 2.0 | 10 mM glycine | >1500 |
| A:CholSO$_4$ 1:1.1 | 4.0 | 10 mM acetate | 86.4 |
| A:CholSO$_4$ 1:1.1 | 5.0 | 10 mM citrate | >1500 |
| A:CholSO$_4$ 1:1.1 | 7.0 | 10 mM Hepes | 456 |
| A:CholSO$_4$ 1:1.1 | 8.0 | 10 mM Hepes | 539 |
| A:CholSO$_4$ 1:1.1 | 10.0 | 10 mM glycine | 615 |
| A:CholSO$_4$ 1:1.1 | 7.0 | 10 mM Hepes:8 M urea | 64.8 |

[a]amphotericin B:lipid ratio.
[b]solvent volume was 0.3 ml of the buffer at 30° C.
[c]Particle diameter was measured after dialysis in distilled water. Values greater than 1500 nm indicate that large particle diameters are present that cannot be accurately measured by dynamic light scattering. In all cases where the diameters were greater than 1500 nm, extensive aggregation and settling of the preparations in the dialysis bag were observed.

With these complexes, changing the ratio of the solvent to aqueous phase, which also increased the concentration of the components, could cause an increase in particle diameter, as was seen in the case of Ny:CholSO$_4$ (Table 4).

TABLE 4

Preparation of Polyene/Lipid Complexes by Solvent Injection

| Component Ratio[a] | pH[b] | Aqueous Phase | Diameter[c] (nm) |
|---|---|---|---|
| Ny:CholSO$_4$ 1:1.1 | 4.0 | 10 mM acetate | 552 |
| Ny:CholSO$_4$ 1:1.1 | 8.0 | 10 mM Hepes | 364 |
| Ny:CholSO$_4$ 1:1[d] | 8.0 | 10 mM Hepes | 500 |
| Ny:Chol 1:1 | 4.0 | 10 mM acetate | >1500 |
| Ny:Chol 1:1 | 8.0 | 10 mM Hepes | >1500 |
| Ny:Chems 1:1 | 4.0 | 10 mM acetate | >1500 |
| Ny:Chems 1:1 | 7.0 | 10 mM Hepes | 45 |
| Ny:Chems 1:1 | 8.0 | 10 mM Hepes | 47 |
| Primaricin:Chol 1:1 | 7.4 | 10 mM Hepes | 1052 |
| Primaricin:Chems 1:1 | 7.4 | 10 mM Hepes | >1500 |

[a]Polyene:lipid ratio. Ny = nystatin.
[b]Solvent volume was 0.3 ml injected into 3.0 ml of the indicated buffer at 30° C.
[c]Particle diameter was measured after dialysis in distilled water. Values greater than 1500 nm indicate that large particle diameters are present that cannot be accurate measured by dynamic light scattering. In all cases where the diameters were greater than 1500 nm, extensive aggregation and settling of the preparations in the dialysis bag were observed.
[d]Solvent volume 1.0 ml injected into 2.0 ml buffer.

The advantage of the injection method for making the polyene:lipid complexes for chemotherapeutic studies (T. Patterson et al., *J Infect Dis* (1989) in press) is that once the injection conditions are established, the procedure is easily scaled up. When the amphotericin B:CholSO$_4$ preparation was scaled up from 3 ml to 50 ml, the same particle size was obtained in the larger scale preparation. A second advantage is that particle sizes less than 200 nm are obtainable with this method. This permits filter sterilization of the resulting formulations.

(B) Other cholesterol derivatives may be used to prepare amphotericin B-lipidic particles. For example, cholesterol phosphate, cholesterol phthalate, cholesterol phosphorylcholine, 3,6,9-trioxaoctan-1-01-cholesterol- 3e-01, and other hydroxy- or amino-cholesterol derivatives, can be dissolved in DMSO, EtOH, methylpyrroline, or MP, combined with amphotericin B in DMSO and injected into buffer to form amphotericin B lipidic particles having diameters less than about 700 nm.

Lipid solutions were prepared using dimyristylphosphatidylcholine:dimyristylphosphatidylglycerol (DMPC:DMPG, 7:3), cholesterol phosphocholine, cholesterol oleate, cholesterol phosphate, cholesteryl phthalate, and cholesterol sulfate in DMSO, DMSO/EtOH, and DMSO/methylpyrroline, and were combined with amphotericin B in DMSO to form solutions 12.5 mM each component (lipid and antibiotic, in 1:1 ratio). The DMSO/methylpyrroline mixtures formed two phases, and were emulsified immediately prior to injection.

An aliquot (0.3 ml) of each mixture was injected into 2.7 ml of 10 mM Tris/lactate buffer (ph 7.0, 0.1 mM EDTA) at 30° C. to form amphotericin B lipidic particles. After injection, the mixture was stirred for five minutes, transferred to dialysis bags, and dialyzed for 48 hours against 100 volumes of 1 mM Tris/lactate (pH 7.0), changed twice. Amphotericin B was quantitatively retained in the particles under these conditions. The diameters of the lipidic particles were determined by laser light scattering, and the means reported in Table 5 below.

TABLE 5

Amphotericin B Lipidic Particles

| Lipid Composition[a] | Solvent | Particle Diameter (nm) |
|---|---|---|
| DMPC:DMPG (7:3) | DMSO/EtOH | 149 |
| cholesterol phosphocholine | It DMSO/EtOH | 659 |
| cholesterol oleate | DMSO/methylpyrroline | 431 |
| cholesterol phosphate | DMSO | 182 |
| cholesterol phthalate | DMSO | 126 |
| cholesterol sulfate | DMSO | 76 |

[a]Each composition contained amphotericin B in a ratio of 1:1 antibiotic:lipid.

Example 4

Encapsulation of Cis-Platinum

Cis-platinum (cisplatin) is another compound widely used in cancer chemotherapy. It is exceedingly soluble in DMSO, and formation of liposomes containing cis-platinum by the DMSO injection technique proceeded easily. Liposomes with diameters between 100 and 220 nm were formed with a variety of lipid compositions (Table 6). With the conditions used here, the final concentration of dis-platinum in the liposome suspension was about 100 µg/ml.

Cis-platinum was dissolved in DMSO at a concentration of 45 mg/ml and added to various lipid compositions to give a final concentration of 7.5 mg/ml (25 mM) in a lipid concentration of between 90 to 135 mM in a DMSO:EtOH mixture of 7:3. Lipid compositions tested include EPC:Chems (2:1) 135 mM; EPC:EPG (7:3) 90 mM and EPC:EPG:Chol (7:3:6) 96.4 mM. At room temperature the lipid-drug mixture was slightly cloudy; the mixture became a clear solution upon a brief heating to 60° C. in a water bath. One ml of the lipid-drug solution was injected into 2 ml of 150 mM NaCl-10 mM Hepes, pH 7.4 (NaCl-Hepes) at 30° C. The liposomes were dialyzed versus 100 volumes of NaCl-Hepes at room temperature for 2 h, and then chromotagraphed on a 1×40 cm Sephadex® G-50 column eluted with the NaCl-Hepes. Cis-platinum concentration was determined by measuring platinum levels in an atomic absorption spectrometer.

TABLE 6

| Preparation of Cis-Platinum Liposomes by Solvent Injection | | |
|---|---|---|
| Components Encapsulation | Efficiency (%)[a] | Diameter (nm)[b] |
| EPC:EPG 7:3 | 7.4 | 169 |
| EPC:EPG:Chol 7:3:6 | 6.9 | 109 |
| EPC:Chems 2:1 | 14.5 | 216 |

[a]Encapsulation efficiency was calculated as the percentage of the initial cis-platinum that remained with the liposome preparation after column separation. The final total lipid in the aqueous phase after column separation was about 20 mm.
[b]Particle diameter was measured after dialysis in 0.1 M NaCl-10 mM Hepes, pH 7.4.

Example 5

Administration of Amphotericin B

Liposomes were prepared with amphotericin B and cholesterol sulfate as described in Example 3. An immunosuppressive neutropenic rabbit model of invasive aspergillosis was used to compare the lipidic particle formulation with free amphotericin B.

Twenty-eight rabbits were immunosuppressed by administration of cyclophosphamide and triamcinolone. The rabbits were then challenged with $10^6$ A. fumigatus. After 24 hours, the rabbits were divided into three treatment/groups: eight rabbits received 4.5 mg/Kg/day free amphotericin B; four rabbits received 7.5 mg/Kg/day free amphotericin B; five rabbits received 6–9 mg/Kg/day amphotericin B lipidic particles (equivalent to 3–4.5 mg/Kg/day amphotericin B); three rabbits received 15 mg/Kg/day amphotericin B lipidic particles (equivalent to 7.5 mg/Kg/day amphotericin B); and eight rabbits were controls.

Acute mortality (death within 24 hours of drug administration) was observed in 4/4 animals receiving 7.5 mg/Kg free amphotericin, and in 3/8 animals receiving 4.5 mg/Kg free amphotericin. No acute mortality was observed in the groups receiving lipidic particle formulations. Treatment was continued for 30 days for the 4.5 mg/Kg free amphotericin B and 6–9 mg/Kg lipidic particle treatment groups.

At the end of the treatment period, the animals were sacrificed, and the liver, kidneys, lung, and brain examined for viable Aspergillis by culturing the organs. The results are reported in Table 7 as the number of sterile organs (free of Aspergillis) per total.

TABLE 7

| Treatment of Aspergillosis | | | | |
|---|---|---|---|---|
| | Organ Cultures (No. Sterile/Total) | | | |
| Group | Liver | Kidney | Lung | Brain |
| Control | 0/8 | 0/8 | 0/8 | 1/3 |
| Free AmpB[a] | 5/5 | 5/5 | 3/5 | 1/5 |
| Lipidic-AmpB[b] | 4/5 | 4/5 | 4/5 | 3/5 |

[a]4.5 mg/Kg/day
[b]6–9 mg/Kg/day

The results indicate that the lipidic particle formulation was as efficacious as the free amphotericin B formulation, while providing significantly less toxicity.

Example 6

Encapsulation of Aqueous Soluble Compounds (A) Encapsulation of sodium phosphonoformate in liposomes of defined size is accomplished using the method of the invention. An 80 mM solution of trisodium phosphonoformate (Sigma Chemical Co.) is used as the receptor phase. One ml of the lipid mixture EPC/EPG/Chol (7:3:6) at 96 mM in DMSO:EtOH (7:3) is injected into 2 ml of phosphonoformate solution. The resulting liposomes are dialyzed against 100 volumes of 140 mM NaCl-10 mM Hepes buffer (pH 7.4) at 4° C., which is changed twice in a 24-hour period. The drug:lipid ratio in the final product is determined using means known in the art (see, e.g., F. Szoka et al., Antimicrob Agents Chemother (1988) 32:858–64). Liposomes having a diameter $\leq 200$ nm are formed.

(B) As demonstrated in Example 1(B) above, one may employ receiving phases having a large variety of solutes without deleterious effect on liposome formation. Any solutes present in the receiving phase are encapsulated upon liposome formation. Thus, one can encapsulate weak acids, weak bases, amino acids, chelating agents, and the like. Solutions of 140 mM sodium carbonate, sodium bicarbonate, sodium acetate, sodium formate, sodium succinate, mono, di and tri sodium citrate, sodium benzoate, sodium salicylate, EDTA, desferroxamine, and the like are prepared and employed as the receptor phase. One ml of lipid solution (EPC, 120 mM) in DMSO:EtOH 7:3 is injected into 2 ml of the receptor phase. The resulting liposome suspensions are dialyzed against 100 volumes of 280 mM lactose solution, changed twice, to provide the encapsulated buffers.

(C) Amino acids are encapsulated as follows: Arginine, glycine, glutamate, lysine, histidine, proline, or other amino acids are prepared at the desired concentration and pH in aqueous solution. One ml of lipid solution (EPC, 120 mM) in DMSO:EtOH 7:3 is injected into 2 ml of the amino acid solution. The resulting liposome suspensions are dialyzed against 100 volumes of 280 mM lactose solution, changed twice, to provide the encapsulated amino acids.

(D) Several compounds may be encapsulated simultaneously. The compounds may be aqueous-soluble, lipid soluble, or may be a mixture of aqueous-soluble and lipid-soluble compounds. For example, an aqueous amino acid solution containing a compound selected from glycine, arginine, ornithine, or another amino acid is prepared at about 100 mM, and the pH adjusted to 7.4. A lipid mixture (1 ml) containing EPC (120 mM) and the endotoxin lipid A (1 mM; J. Dijkstra et al., J Immunol (1987) 138:2663–71) is injected into 2 ml of aqueous phase, and the resulting liposome suspension is dialyzed against 100 volumes of 0.14M NaCl. The liposomes contain an amino acid in the aqueous phase, and lipid A in the lipid phase, and present a diameter of $\leq 200$ nm.

(E) A wide spectrum of compounds are encapsulated using the method of the invention. Suitable compounds include, without limitation, fluorescent molecules, radiocontrast agents, radioactive isotopes and compounds, paramagnetic compounds, spin labels, flavin containing compounds, antibiotics such as aminoglycosides, antiviral compounds such as azidothymidine or deoxycytidine and their phosphorylated derivatives, nucleotides and their phosphorylated derivatives, carbohydrates, peptides such as vasopressin, oxytocin, lutenizing hormone releasing hormone, muramylpeptide derivatives and analogs, calcitonin, insulin, protease inhibitors such as captorpil and leupeptin, reinin inhibitors, oligonucleotides and their derivatives (see, e.g., G. Zon, Pharmaceut Res (1988) 5:539–49), ribonucleic acids, deoxyribonucleic acids, modified nucleic acids, proteins such as superoxide dismutase, human growth hormone, interferons, interleukins such as IL-1, IL-2, and the like. The method of the invention advantageously forms liposomes or lipidic particles under low shear conditions, forming particles with a well-defined size and high concentration.

Example 7

Compositions Formed by Aqueous Injection

A mixture of lipids consisting of 300 μmoles of egg phosphatidylcholine and 50 μmoles of phosphatidylglycerol was dissolved in 1.5 ml of absolute ethanol. 150 μmoles of cholesterol was dissolved in 2-methylpyrollidone and the volume adjusted to 3.2 ml by the addition of 2-methylpyrollidone. The phospholipid and cholesterol solutions were mixed, resulting in 100 μmole lipid/ml of solvent. The lipid composition had a mole ratio of egg phosphatidylcholine-:phosphatidylgylcerol:cholesterol of 6:1:3 dissolved in a solvent consisting of a 2:1 (volume/volume) ratio of 2-methylpyrollidone:ethanol (the "stock lipid solution").

Three injections were performed that illustrate the ability to control diameter of the liposomes by injecting the aqueous phase into the organic phase:

(A) 0.5 ml of the stock lipid solution was injected into 2.5 ml of a 0.135M NaCl-10 mM Hepes pH 7.4 solution that was rapidly stirred by a magnetic stirring bar.

(B) 0.5 ml of stock lipid solution was added to 1.5 ml of a DMSO/ethanol:2/1 mixture (the "working DMSO lipid solution"). Then 1.0 ml of the 0.135M NaCl-10 mM Hepes ph 7.4 buffer was injected into the 2.0 ml working DMSO lipid solution as it was rapidly stirred by a magnetic stirring bar.

(C) 0.5 ml of stock lipid solution was added to 1.5 ml of a 2-methylpyrollidone:ethanol (2:1) mixture (working lipid solution). Then 1.0 ml of 0.135M NaCl-10 mM Hepes pH 7.4 buffer was injected into 2.0 ml working lipid solution as it was rapidly stirred by a magnetic stirring bar.

Lipid suspensions A–C were then transferred to individual dialysis bags, sealed and dialyzed against two consecutive 1250 ml volumes of 0.135M NaCl-2 mM Hepes, pH 7.4 buffer held at 4° C. over a 24-hour period. The diameter of the resulting liposome dispersions were measured by laser light scattering.

TABLE 8

| Injection of Aqueous Phase into Organic Phase | | | |
|---|---|---|---|
| Sample | Description | Diameter (nm) | Polydispersity |
| A | organic to aqueous | 188 | 0.21 |
| B | aqueous into organic | 392 | 0.15 |
| C | aqueous into organic | 532 | 0.56 |

Thus, at the same total lipid concentration in the final injection reaction, liposomes of different diameters can be prepared.

Example 8

To encapsulate DNA via the solvent injection technique, 120 μg calf thymus DNA was dissolved per 1 ml of 30 mM Tris/Cl, ph 8.5 buffer. A lipid stock solution of palmitoyloleoylphosphatidylethanolamine:cholesterolhemisuccinate (2:1 molar ratio) was prepared in a DMSO:ethanol (2:1 volume/volume) solvent mixture.

Six separate injections were done with various conditions of lipid concentration in the organic receptor phase and phase volumes. In the first three injections, 1 ml of the aqueous DNA solution was injected into 1.0 ml of the DMSO/ethanol lipid solution at three lipid concentrations (1, 5 and 10 mM total lipid). The organic phase containing the lipid was rapidly stirred by a magnetic stirring bar during the injection. The resulting liposome dispersions were placed in individual dialysis bags and dialyzed overnight at 4° C. against 1 liter of 135M NaCl-2 mM Hepes (pH 7.4). After dialysis, the diameter of the resulting liposomes was measured by laser light scattering. The diameter for each 1:1 preparation (in nm) is shown in Table 9.

The second three injections consisted of 0.5 ml of aqueous DNA solution injected into 1.5 ml of the DMSO/ethanol lipid solution at three lipid concentrations (1, 5, 10 mM total lipid). The organic phase containing the lipid was rapidly stirred by a magnetic stirring bar during the injection. The resulting liposome dispersions were placed in individual dialysis bags and dialyzed overnight at 4° C. against 1 liter of 135M NaCl-2 mM Hepes (ph 7.4). After dialysis, the diameter of the resulting liposomes was measured by laser light scattering. The results for these 1:3 preparations are shown in Table 9.

TABLE 9

| Diameter of Resulting Liposomes Following Injection of DNA in the Aqueous Phase into an Organic Solution of Lipids | | | |
|---|---|---|---|
| Phase Ratio (aqueous: organic) | Concentration of Lipid (mM) | | |
|  | 1 | 5 | 10 |
| 1:1 | 125 | 155 | 193 |
| 1:3 | 231 | 237 | 291 |

Thus, injection of the aqueous phase into the organic phase also results in the preparation of liposomes by this technique.

What is claimed is:

1. A product of the process for preparing a lipid suspension of particle size less than about 10,000 nm in diameter encapsulating a therapeutically, pharmaceutically or diagnostically useful compound, which process comprises:

dissolving said useful compound and an encapsulating amount of a suitable lipid in a sufficient amount of a solvent mixture comprising a non-halogenated hydrocarbon aprotic solvent to provide a compound/lipid solution; and extruding said compound/lipid solution through a suitably-sized aperture into an aqueous solution to form a lipid-compound suspension of particle size less than about 10,000 nm in diameter.

2. The product-by-process of claim 1 further comprising a lipid suspension of liposomes and a useful compound selected from the group consisting of cisplatin, doxorubicin, epinephrine, mebendazole, niridazole, and taxol.

3. The product-by-process of claim 1 further comprising a lipid suspension of lipidic particles and a useful compound selected from the group consisting of amphotericin B, nystatin, and primaricin.

4. The product-by-process of claim 1 wherein the lipid-compound suspension has a particle size between 20 and 600 μm and wherein the therapeutically, pharmaceutically, or diagnostically useful compound is amphotericin B.

* * * * *